United States Patent
Nagareda et al.

(10) Patent No.: US 9,172,026 B2
(45) Date of Patent: Oct. 27, 2015

(54) PIEZOCERAMIC COMPOSITION AND METHOD FOR MANUFACTURING THE SAME

(75) Inventors: Kenji Nagareda, Aichi (JP); Dunzhuo Dong, Aichi (JP)

(73) Assignee: HONDA ELECTRONICS CO., LTD., Aichi (JP)

( * ) Notice: Subject to any disclaimer, the term of this patent is extended or adjusted under 35 U.S.C. 154(b) by 0 days.

(21) Appl. No.: 13/809,743

(22) PCT Filed: Mar. 2, 2012

(86) PCT No.: PCT/JP2012/056048
§ 371 (c)(1),
(2), (4) Date: Jan. 11, 2013

(87) PCT Pub. No.: WO2013/128651
PCT Pub. Date: Sep. 6, 2013

(65) Prior Publication Data
US 2014/0367605 A1    Dec. 18, 2014

(51) Int. Cl.
| | |
|---|---|
| *H01L 41/187* | (2006.01) |
| *C04B 35/495* | (2006.01) |
| *H01L 41/43* | (2013.01) |
| *C01G 30/00* | (2006.01) |
| *C01G 33/00* | (2006.01) |
| *C01G 35/00* | (2006.01) |
| *G01N 23/20* | (2006.01) |

(52) U.S. Cl.
CPC ............ *H01L 41/1878* (2013.01); *C01G 30/00* (2013.01); *C01G 33/00* (2013.01); *C01G 35/00* (2013.01); *C04B 35/495* (2013.01); *G01N 23/2005* (2013.01); *H01L 41/1873* (2013.01); *H01L 41/43* (2013.01); *C04B 2235/3201* (2013.01); *C04B 2235/3203* (2013.01); *C04B 2235/3251* (2013.01); *C04B 2235/3272* (2013.01); *C04B 2235/3294* (2013.01); *C04B 2235/3298* (2013.01); *C04B 2235/5436* (2013.01); *C04B 2235/768* (2013.01); *C04B 2235/79* (2013.01); *C04B 2235/80* (2013.01)

(58) Field of Classification Search
USPC ...................................... 252/62.9 R; 501/134
See application file for complete search history.

(56) References Cited

U.S. PATENT DOCUMENTS

2009/0020726 A1    1/2009  Uraki et al.

FOREIGN PATENT DOCUMENTS

| | | |
|---|---|---|
| JP | 2002-284574 | 10/2002 |
| JP | 2004-115293 | 4/2004 |
| JP | 2006-315909 | 11/2006 |
| JP | 2007-076926 | 3/2007 |
| JP | 2008-162889 | 7/2008 |
| JP | 2008-207999 | 9/2008 |
| JP | 4326374 | 9/2009 |
| JP | 2010-030814 | 2/2010 |
| JP | 2010-053021 | 3/2010 |
| JP | 2011-109037 | 6/2011 |
| JP | 2011-211139 | 10/2011 |
| WO | 2008/078703 | 7/2008 |

OTHER PUBLICATIONS

Axelsson Anna-Karin, "Synthesis, Sintering . . . KTaO3 Ceramics", J Am Ceram Soc., Aug. 2009, vol. 92, No. 8, pp. 1773-1778.

*Primary Examiner* — Carol M Koslow
(74) *Attorney, Agent, or Firm* — Clark & Brody

(57) ABSTRACT

A piezoceramic composition comprises, as the main phase, a crystalline phase of a perovskite structure signified as formula $ABO_3$, with Element A consisting of one or more elements selected from among K (potassium), Na (sodium) and Li (lithium) and with Element B consisting of one or more elements selected from among Nb (niobium), Ta (tantalum) and Sb (antimony), with Elements A and B comprising other elements as additives. An X-ray diffraction profile of crushed particles of the piezoceramic composition that are 10 μm or less in diameter has a diffraction peak indicating the presence of the main (single) phase as well as a heterogeneous phase of a crystalline structure signified as formula $A_sB_tO_u$ ($s<t<u$) but not belonging to the perovskite structure.

4 Claims, 3 Drawing Sheets

PIEZOCERAMIC COMPOSITION AND METHOD FOR MANUFACTURING THE SAME

TECHNICAL FIELD

This invention relates to an alkaline niobate-piezoceramic composition, and to a method for manufacturing the same, for the making of actuators, ultrasonic sensors, ultrasonic transducers or the like.

TECHNICAL BACKGROUND

Piezoceramic composition is used as a piezoelectric element in the making of actuators, ultrasonic sensors, ultrasonic transducers or the like. Since piezoceramic composition has excellent piezoelectric property, lead zirconate titanate (PZT) or the like containing a lead compound has already been practically used. However, due to a concern that such piezoceramic composition containing a lead compound may negatively affect the environment, a lead-free piezoceramic composition is now attracting attention and is being researched and developed. The alkaline niobate-piezoceramic composition, as disclosed in Patent References 1 to 3 below, is such a piezoceramic composition free of a lead compound.

The piezoceramic composition as disclosed in Patent Documents 1 to 3 is a perovskite compound signified as composition formula $ABO_3$ that contains potassium and sodium as elements of Site A and contains niobium and tantalum as elements of Site B.

PRIOR ART DOCUMENTS

Patent Document 1: JP Patent No. 4326374
Patent Document 2: JP Patent No. 4398635
Patent Document 3: JP-A-2008-162889

DISCLOSURE OF THE INVENTION

Problems to be Resolved by the Invention

It is commonly recognized that in manufacturing an alkaline niobate-piezoceramic composition that difficulties in obtaining stability and reproducibility of the piezoelectric property exist as well other problems such as weighing errors caused by the hydroscopic property of the potassium material used as the initial ingredient and of potassium-volatilization caused during the sintering process or the like. Thus, it is now required that technology be developed to manufacture consistently at a low cost products having a good piezoelectric property (especially ones having a radial electromechanical coefficient of 0.4 or more) and ones having the property of less unevenness.

This invention is achieved in light of the aforementioned problems to provide a piezoceramic composition having a good piezoelectric property and the property of less unevenness to provide a method for manufacturing piezoceramic products at a low cost.

Means of Solving the Problems

To solve the aforementioned problems, the first aspect of this invention refers to a piezoceramic composition comprising, as the main phase, a crystalline phase of a perovskite structure signified as formula $ABO_3$, with Element A consisting of one or more elements selected from among K (potassium), Na (sodium) and Li (lithium) and with Element B consisting of one or more elements selected from among Nb (niobium), Ta (tantalum) and Sb (antimony), with Elements A and B comprising other elements as additives, wherein an X-ray diffraction profile of the powder sample that is crushed until the particles of the piezoceramic composition are 10 μm or less in diameter has a diffraction peak indicating the presence of the main (single) phase as well as a heterogeneous phase of a crystalline structure signified as formula $A_sB_tO_u$ (s<t<u) but not belonging to the perovskite structure (hereinafter referred to as heterogeneous phase $A_sB_tO_u$), with the intensity ratio $(v)=I_{max}(2\theta=29.3°)/I_{max}(2\theta=31.8°)$ and defined as $0<v\leq 0.088$, with the ratio of the main peak diffraction intensity indicating that the aforementioned heterogeneous phase is near $2\theta=29.3°$ and that the main peak diffraction intensity is near $I_{max}(2\theta=31.8°)$.

According to the first aspect of this invention, the piezoceramic composition including heterogeneous phase $A_sB_tO_u$ is produced, and the gross composition indicates a rich Site B (Element B excessive) resulting in A/B=0.95 to 0.98. Regarding the piezoceramic composition of this invention, the rate of A-site defects on the main (single) phase is about 2%, which is the most that can occur on Site A. Thus, alternatively, heterogeneous phase $A_sB_tO_u$ is produced as a by-product. Also, if the piezoceramic composition contains no metallic elements other than K, Na, Li, Nb, Ta and Sb, then the A-site defect tolerance will decrease remarkably. Contrarily, if a small amount of metallic elements are added, then point defects will be introduced, thus enabling the A-site defect tolerance to increase properly. When increasing the A-site defects on the main (single) phase of this invention, the preciseness of the sintered compact (ceramics) will also increase, thus improving the piezoelectric property. Also, if there is too much deficiency of Element A, the amount of A-site defects will reach its tolerance level (of approximately 2%) and never increase more. Thus, alternatively, heterogeneous phase $A_sB_tO_u$ will be produced.

Manufacturing piezoceramic composition so that it is sintered to the amount of A-site defects corresponding to the limit at which heterogeneous phase $A_sB_tO_u$ is not produced makes it possible to obtain a favorable piezoceramic property. However, it is difficult to produce such a piezoceramic composition at the desired limited ratio at which heterogeneous phase $A_sB_tO_u$ is not produced. Especially in mass-producing such piezoceramic composition, due to unevenness of the temperature and the atmosphere within the firing furnace, it is difficult to adjust the whole piezoceramic composition to be sintered to the desired amount of A-site defects. Once there exists a discrepancy in the composition ratio, so that heterogeneous phase $A_sB_tO_u$ is not produced, such fluctuation of the composition ratio directly causes an increase or decrease in the amount of A-site defects, thus resulting in unevenness of the reproducibility of the piezoceramic property of each production lot.

On the other hand, the piezoceramic composition of this invention is of a ratio containing heterogeneous phase $A_sB_tO_u$, so that the intensity ratio v of diffraction intensity $I_{max}$ ranges at $0<v\leq 0.088$. Therefore, the radial electromechanical-coupling coefficient becomes 0.4 or more, thereby obtaining a favorable piezoceramic composition of an industrially stable piezoelectric property. Specifically, if there occurs a discrepancy in the composition ratio of the piezoceramic composition of this invention, the production ratio of heterogeneous phase $A_sB_tO_u$ will fluctuate, thus having less effect on the piezoceramic property of said composition. However, the fluctuation of the A-site defects on the main (single) phase will lessen. In other words, the production rate of heterogeneous phase $A_sB_tO_u$, which has a low impact on the property, will become moderate compared to the uneven sintering of the composition, thus controlling the composition discrepancy of the A/B ratio on the main (single) phase (the $ABO_3$-perovskite structured crystalline phase) that has great effect on sinterability and property, so that the piezoceramic composition in the firing furnace is fully sintered to a condition thereof the A-site defects on the main (single) phase is nearly maximum. Therefore, the property of unevenness of said piezoceramic composition is kept low, thus making it possible to mass-produce the piezoceramic composition in a highly efficient manner.

The second aspect of this invention is that the aforementioned heterogeneous phase is an oxide comprising more than 1.5 times but less than 4.0 times of Element B than Element A.

According to the second aspect of this invention, the heterogeneous phase comprising Element B of more than 1.5 times but less than 4.0 times than Element A makes it possible to manufacture this piezoceramic composition having an industrially stable piezoelectric property.

The third aspect of this invention is that the heterogeneous phase of the first and second aspects of this invention is an oxide signified as $A_6B_{10.8}O_{30}$ of a weight ratio (w) of $0\% < w \leq 6.0\%$.

According to the third aspect of this invention, there exists an appropriate amount of the heterogeneous phase signified as formula $A_6B_{10.8}O_{30}$ that allows for manufacturing said piezoceramic composition having an industrially stable piezoelectric property. Also, the heterogeneous phase $A_6B_{10.8}O_{30}$ is crystallized in the tetragonal system of low piezoelectricity at room temperature, so that if the production ratio of heterogeneous phase $A_6B_{10.8}O_{30}$ increases, the piezoelectric property of said piezoceramic composition would decrease. Contrarily, heterogeneous phase $A_6B_{10.8}O_{30}$ is produced at a weight ratio of 6% or less, thus controlling the decrease in piezoelectric property caused by an increase in the production ratio of the heterogeneous phase.

The fourth aspect of this invention is that according to either one of the first to third aspects of this invention, the aforementioned mixture of added metallic elements Bi (bismuth) and Fe (iron) is described as Formula $(1-z) ABO_3+z (0.5Bi_2O_3+0.5Fe_2O_3)$ of which the total composition ratio is one (1) and z ranges at $0 < z \leq 0.02$.

Adding an appropriate amount of Bi (bismuth) and Fe (iron), according to the fourth aspect of this invention, produces a piezoceramic composition of good piezoelectric property even if there exists no Ta (tantalum) as Element B. Ta (tantalum) is an ingredient that is relatively costly compared to Nb (niobium) and Sb (antimony), so that manufacturing a piezoceramic composition without Ta reduces the manufacturing cost.

The fifth aspect of this invention refers to a method for manufacturing the piezoceramic composition according to either the first to fourth aspects of this invention by conducting a calcining process and then a sintering process, and is characterized (following the calcining process) by an X-ray diffraction procedure being done to obtain an X-ray diffraction profile of the calcined powder obtained by crushing the composition, and that a composition-adjustment procedure be done according to the composition ratio identified in the X-ray diffraction procedure, and that based on the X-ray diffraction profile, the sintering process is done by using the calcined powder that had gone through the composition-adjustment procedure.

According to the fifth aspect of this invention, based on the X-ray diffraction profile of the calcined powder, the production ratio of the different phase $A_sB_tO_u$ is identified. Then, composition adjustment is done according to the production ratio. In this case, it is still possible to use the calcined powder that had ranged outside the favorable production ratio of the different phase $A_sB_tO_u$, so that composition adjustment can be done to obtain the most appropriate composition ratio. Especially regarding the alkaline-niobate ingredient, errors in weighing caused by the hydroscopic property of the potassium $K_2CO_3$ powder may produce a discrepancy in the composition. To resolve such errors, it is firstly required that an X-ray diffraction be done of the calcined powder that had been obtained by sintering the mixture at 800 to 900 degrees Celsius to determine the production status of heterogeneous phase $A_sB_tO_u$ to clarify the composition discrepancy that had been caused during the calcining stage. Secondly, it is required that the composition be mixed to get the required production amount of heterogeneous phase $A_sB_tO_u$. Then, if necessary, another calcining is to be done, with a binder added to enhance the further sintering. Eventually then the composition discrepancy regarding the materials will be resolved. Thus, the calcined powder that had ranged outside the favorable production ratio of the heterogeneous phase need not be disposed and is thus more likely to produce the piezoceramic composition. Therefore, the loss of ingredients in disposing of them shall be reduced, thus eventually reducing the cost of manufacturing said piezoceramic composition.

Effects of the Invention

As described above, the aspects 1 to 4 of this invention provide a piezoceramic composition having a favorable piezoelectric property and the property of less unevenness. The fifth aspect of this invention also makes it possible to manufacture said piezoceramic composition at a low cost.

MODES FOR CARRYING OUT THE INVENTION

First Embodiment

Hereinafter, the preferred embodiments of the alkaline niobate-piezoceramic composition of this invention are described with reference to the drawings.

Figure 1:
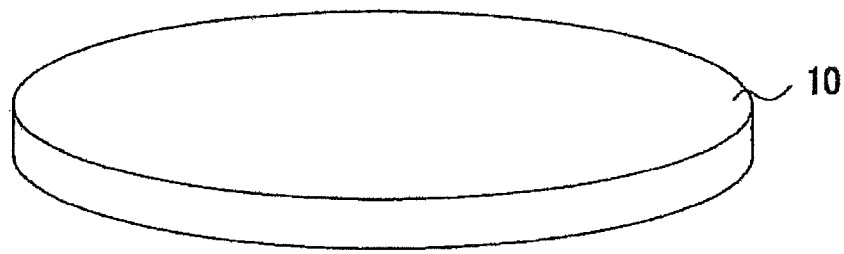
FIG. 1 is a diagrammatic perspective showing the piezoceramic composition as the first embodiment of this invention.

FIG. 1 is a diagrammatic perspective of Piezoceramic Composition 10, the embodiment of this invention, formed into a disk 15 mm in diameter and 1 mm thick, which piezoceramic composition for instance is used as an ultrasonic sensor configured in an ultrasonic flow meter, as well as a knocking sensor in an engine or as an ultrasonic oscillator in an ultrasonic washing machine or the like. As such, the shape and size of Piezoceramic Composition 10 can vary according to its intended use.

Piezoceramic Composition 10, the embodiment of this invention, comprises as the main phase a crystalline phase of a perovskite structure signified as formula $ABO_3$, as well as comprising K (potassium), Na (sodium) and Li (lithium) as elements of Site A and comprising at least Nb (niobium), Ta (tantalum) and Sb (antimony) as elements of Site B. Piezoceramic Composition 10 also comprises the metallic elements Bi (bismuth) and Fe (iron) which are different than the elements of Sites A and B.

Hereinafter, the method for manufacturing Piezoceramic Composition 10 is described.

Firstly, prepare the base powder (pure grade: 99% or more) of $K_2CO_3$, $Na_2CO_3$, $Li_2CO_3$, $Nb_2O_5$, $Ta_2O_5$, $Sb_2O_3$, $Bi_2O_3$ and $Fe_2O_3$. Then, to fulfill each composition of Working Examples 1 to 16 and Comparative Examples 1 to 21, as shown in Chart 1, weigh the base powder containing each metallic element and obtain slurry by ball-milling the powder in alcohol for 24 hours. The type of base powder (compound) to be used is not strictly limited. However, dioxide, carbonate or the like of each metallic element can favorably be used.

Secondly, dry the slurry and temporarily sinter it at 900 degrees Celsius for three hours. Then, crush the slurry by ball-milling it for 24 hours. Then, add polyvinyl alcohol, a binder, to pelletize the slurry. After pelletization, press the powder-slurry at 2 $kN/cm^2$ into a disk 18 mm in diameter and 2 mm thick. Then, sinter the disk at 1,000 to 1,200 degrees Celsius for 2.5 hours to maximize its density.

Thirdly, simultaneously grind the top and bottom of each sintered disk until they are 15 mm in diameter and 1 mm thick, as shown in FIG. 1. Apply silver paste to the top and bottom of the disks and bake them at 500 degrees Celsius to form in them opposite electrodes. In silicone oil at 130 degrees Celsius, apply a direct-current voltage of 3 kV/mm between said electrodes of the disks to polarize them from top to bottom, thereby obtaining Piezoceramic Composition 10.

CHART 1

| | Chemical Formula $(1-z)[(K_{0.44}Na_{0.52}Li_{0.04})_a (Nb_{1-x-y}Ta_xSb_y)O_3] + z(0.5Bi_2O_3 + 0.5Fe_2O_3)$ | | | |
|---|---|---|---|---|
| | a | x | y | z |
| Comparative Example 1 | 1.01 | 0.10 | 0.04 | 0.008 |
| Comparative Example 2 | 1.00 | 0.10 | 0.04 | 0.008 |
| Comparative Example 3 | 0.99 | 0.10 | 0.04 | 0.008 |
| Comparative Example 4 | 0.98 | 0.10 | 0.04 | 0.008 |
| Working Example 1 | 0.97 | 0.10 | 0.04 | 0.008 |
| Working Example 2 | 0.96 | 0.10 | 0.04 | 0.008 |
| Comparative Example 5 | 0.94 | 0.10 | 0.04 | 0.008 |
| Comparative Example 6 | 0.90 | 0.10 | 0.04 | 0.008 |
| Comparative Example 7 | 0.85 | 0.10 | 0.04 | 0.008 |
| Working Example 3 | 0.98 | 0.05 | 0.04 | 0.008 |
| Working Example 4 | 0.97 | 0.05 | 0.04 | 0.008 |
| Working Example 5 | 0.96 | 0.05 | 0.04 | 0.008 |
| Working Example 6 | 0.98 | 0.00 | 0.04 | 0.008 |
| Working Example 7 | 0.97 | 0.00 | 0.04 | 0.008 |
| Comparative Example 8 | 0.96 | 0.00 | 0.04 | 0.008 |
| Comparative Example 9 | 0.98 | 0.10 | 0.04 | 0 |
| Comparative Example 10 | 1.00 | 0.00 | 0.04 | 0 |
| Comparative Example 11 | 0.98 | 0.00 | 0.04 | 0 |
| Working Example 8 | 0.98 | 0.00 | 0.04 | 0.004 |
| Working Example 9 | 0.98 | 0.00 | 0.04 | 0.008 |
| Working Example 10 | 0.97 | 0.00 | 0.04 | 0.008 |
| Comparative Example 12 | 0.96 | 0.00 | 0.04 | 0.008 |
| Comparative Example 13 | 0.98 | 0.00 | 0.04 | 0.012 |
| Working Example 11 | 0.97 | 0.00 | 0.04 | 0.012 |
| Comparative Example 14 | 0.98 | 0.00 | 0.04 | 0.016 |
| Working Example 12 | 0.97 | 0.00 | 0.04 | 0.016 |
| Working Example 13 | 0.96 | 0.00 | 0.04 | 0.016 |
| Comparative Example 15 | 0.97 | 0.00 | 0.04 | 0.02 |
| Working Example 14 | 0.96 | 0.00 | 0.04 | 0.02 |
| Working Example 15 | 0.95 | 0.00 | 0.04 | 0.02 |
| Comparative Example 16 | 0.96 | 0.00 | 0.04 | 0.024 |
| Comparative Example 17 | 0.97 | 0.00 | 0.04 | 0.032 |
| Comparative Example 18 | 0.96 | 0.00 | 0.04 | 0.032 |
| Comparative Example 19 | 0.95 | 0.00 | 0.04 | 0.032 |
| Comparative Example 20 | 1.00 | 0.00 | 0.00 | 0.008 |
| Comparative Example 21 | 0.98 | 0.00 | 0.00 | 0.008 |
| Working Example 1 | 60.96 | 0.00 | 0.00 | 0.008 |

Each sample of Piezoceramic Composition 10 was produced regarding Working Examples 1 to 16 and Comparative Examples 1 to 21.

The inventors of this invention measured the electric and unevenness property of each lot and measured the process-capability index $C_{pk}$ regarding Working Examples 1 to 16 and Comparative Examples 1 to 21. The measurements are shown in Chart 2, below. Using an impedance analyzer (Agilent 4294A) on the embodiment of this invention, the radial-electric property of electromechanical-coupling coefficient Kp, relative permittivity $\epsilon_{33}^T/\epsilon_0$ and dielectric loss tan δ, was measured at 25 degrees Celsius. One hundred samples were measured, of which the average values are shown in Chart 2. The standard deviation of electromechanical-coupling coefficient Kp of each lot was calculated for the unevenness property, and by using the average value of all the lots, the process capability index $C_{pk}$ under the standard of Kp≥0.4 was calculated.

CHART 2

| | Electrical property at 25 degrees Celsius (° C.) | | | Unevenness property of the same lot Standard | Process Capability |
|---|---|---|---|---|---|
| | Kp | $\epsilon_{33}^T/\epsilon_0$ | tan δ | deviation of Kp | Index $C_{pk}$ |
| Comparative Example 1 | 0.192 | 1107 | 0.0402 | 0.0032 | −21.72 |
| Comparative Example 2 | 0.181 | 1089 | 0.0801 | 0.0089 | −8.19 |
| Comparative Example 3 | 0.336 | 1217 | 0.0267 | 0.0247 | −0.86 |
| Comparative Example 4 | 0.435 | 1552 | 0.0175 | 0.0121 | 0.96 |
| Working Example 1 | 0.423 | 1510 | 0.0187 | 0.0007 | 10.89 |
| Working Example 2 | 0.405 | 1471 | 0.0194 | 0.0010 | 1.64 |
| Comparative Example 5 | 0.345 | 1303 | 0.0215 | 0.0018 | −10.27 |
| Comparative Example 6 | 0.241 | 1017 | 0.0257 | 0.0017 | −31.25 |
| Comparative Example 7 | 0.143 | 764 | 0.0256 | 0.0018 | −47.53 |
| Working Example 3 | 0.481 | 1440 | 0.0217 | 0.0011 | 24.57 |
| Working Example 4 | 0.449 | 1380 | 0.0231 | 0.0006 | 27.33 |

CHART 2-continued

|  | Electrical property at 25 degrees Celsius (° C.) | | | Unevenness property of the same lot Standard | Process Capability |
| --- | --- | --- | --- | --- | --- |
|  | Kp | $\epsilon_{33}^T/\epsilon_0$ | tan δ | deviation of Kp | Index $C_{pk}$ |
| Working Example 5 | 0.414 | 1304 | 0.0230 | 0.0005 | 9.45 |
| Working Example 6 | 0.481 | 1086 | 0.0242 | 0.0008 | 33.88 |
| Working Example 7 | 0.427 | 1008 | 0.0248 | 0.0007 | 13.02 |
| Comparative Example 8 | 0.372 | 924 | 0.0258 | 0.0013 | −7.20 |
| Comparative Example 9 | 0.325 | 1243 | 0.0606 | 0.0011 | −22.63 |
| Comparative Example 10 | 0.211 | 633 | 0.2580 | 0.0076 | −8.30 |
| Comparative Example 11 | 0.345 | 868 | 0.1790 | 0.0052 | −3.54 |
| Working Example 8 | 0.459 | 958 | 0.0257 | 0.0006 | 32.70 |
| Working Example 9 | 0.481 | 1105 | 0.0230 | 0.0005 | 53.81 |
| Working Example 10 | 0.415 | 985 | 0.0247 | 0.0008 | 6.37 |
| Comparative Example 12 | 0.394 | 893 | 0.0252 | 0.0012 | −1.75 |
| Comparative Example 13 | 0.452 | 1301 | 0.0237 | 0.0142 | 1.22 |
| Working Example 11 | 0.480 | 1390 | 0.0232 | 0.0004 | 66.51 |
| Comparative Example 14 | 0.427 | 1305 | 0.0372 | 0.0148 | 0.62 |
| Working Example 12 | 0.487 | 1501 | 0.0237 | 0.0003 | 96.33 |
| Working Example 13 | 0.459 | 1450 | 0.0241 | 0.0009 | 21.84 |
| Comparative Example 15 | 0.446 | 1434 | 0.0253 | 0.0128 | 1.19 |
| Working Example 14 | 0.421 | 1372 | 0.0264 | 0.0005 | 14.06 |
| Working Example 15 | 0.432 | 1421 | 0.0242 | 0.0007 | 15.04 |
| Comparative Example 16 | 0.386 | 1282 | 0.0268 | 0.0008 | −5.94 |
| Comparative Example 17 | 0.167 | 2205 | 0.5030 | 0.0012 | −64.60 |
| Comparative Example 18 | 0.192 | 1211 | 0.0654 | 0.0013 | −53.43 |
| Comparative Example 19 | 0.280 | 1273 | 0.0279 | 0.0015 | −26.64 |
| Comparative Example 20 | 0.301 | 744 | 0.2040 | 0.0086 | −3.83 |
| Comparative Example 21 | 0.375 | 640 | 0.1730 | 0.0026 | −3.26 |
| Working Example 16 | 0.408 | 446 | 0.1440 | 0.0018 | 1.48 |

Figure 2:
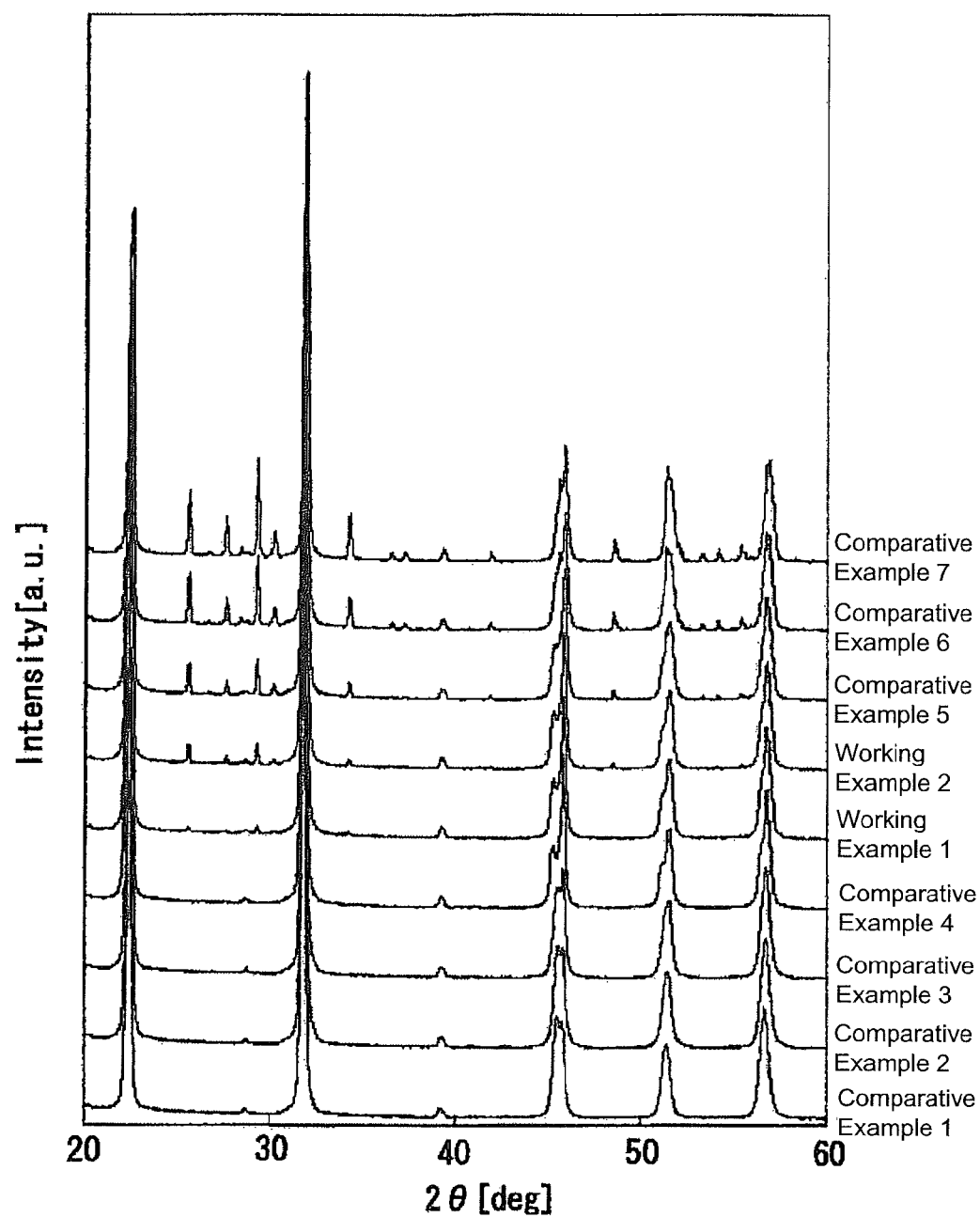
FIG. 2 is a graph describing the X-ray diffraction profile of the piezoceramic composition powder sample of Embodiments 1 and 2, as well as Comparative Examples 1 to 7.

The inventors of this invention conducted an XRD analysis regarding Piezoceramic Composition 10 of Working Examples 1 to 16 and Comparative Examples 1 to 21 by using an X-ray diffractometer (Rigaku Corporation SmartLab®, X-ray source: Cu Kα, Detector: D-TEX Ultra). FIG. 2 shows an example of the X-ray diffraction profile. Here, Piezoceramic Composition 10, of which the electrode had not yet been formed or the electrode had been removed by grinding, was crushed in a mortar to granular powder of 10 μm or less in diameter. The XRD analysis was done by setting the sample powder on the measuring holder of an X-ray diffractometer and specifically done by using the θ-2θ method and concentrated-beam method ranging at 2θ=5 to 100° and at the scanning speed of 4°/min at the interval of 2θ=0.2°. The XRD analysis need not be limited to the aforementioned methods as long as the presence or absence of heterogeneous phase $A_sB_tO_u$ can correctly be determined.

Regarding the X-ray diffraction profile of Working Examples 1 to 16 and Comparative Examples 1 to 21 (See FIG. 2) obtained by the XRD analysis, the main peak was identified near 2θ=31.8° showing the main (single) phase $ABO_3$. Whereas the peak showing the heterogeneous phases of $A_sB_tO_u$ such as $A_6B_{10.8}O_{30}$, $A_4B_6O_{17}$ or the like was near 2θ=29.3°. However, that peak was identified in some powder samples but not identified in other powder samples. (See Chart 3)

CHART 3

|  | Intensity ratio of XRD diffraction peak | | | $A_6B_{10.8}O_{30}$ production ratio w(wt %) |
| --- | --- | --- | --- | --- |
|  | $I_{max}$ (2θ = 29.3°) | $I_{max}$ (2θ = 31.8°) | v = $I_{max}$(2θ = 29.3°)/ $I_{max}$(2θ = 31.8°) |  |
| Comparative Example 1 | — | 186122 | — | 0.0 |
| Comparative Example 2 | — | 181212 | — | 0.0 |
| Comparative Example 3 | — | 183253 | — | 0.0 |
| Comparative Example 4 | — | 162357 | — | 0.0 |
| Working Example 1 | 2568 | 165793 | 0.0155 | 1.9 |
| Working Example 2 | 8922 | 160401 | 0.0556 | 5.3 |
| Comparative Example 5 | 15446 | 106693 | 0.1448 | 10.4 |
| Comparative Example 6 | 30317 | 157240 | 0.1928 | 22.4 |
| Comparative Example 7 | 37721 | 123535 | 0.3053 | 32.4 |
| Working Example 3 | 1370 | 160109 | 0.0086 | 1.1 |
| Working Example 4 | 6032 | 161421 | 0.0374 | 3.6 |
| Working Example 5 | 9329 | 106114 | 0.0879 | 6.0 |
| Working Example 6 | 1789 | 119718 | 0.0149 | 1.0 |
| Working Example 7 | 4674 | 150142 | 0.0311 | 3.1 |
| Comparative Example 8 | 9967 | 112838 | 0.0883 | 6.5 |
| Comparative Example 9 | 3458 | 160393 | 0.0216 | 2.0 |
| Comparative Example 10 | — | 203766 | — | 0.0 |
| Comparative Example 11 | — | 171570 | — | 0.0 |
| Working Example 8 | 865 | 192193 | 0.0045 | 4.1 |

CHART 3-continued

|  | Intensity ratio of XRD diffraction peak | | | $A_6B_{10.8}O_{30}$ production ratio w(wt %) |
|---|---|---|---|---|
|  | $I_{max}$ ($2\theta = 29.3°$) | $I_{max}$ ($2\theta = 31.8°$) | $v = I_{max}(2\theta = 29.3°)/I_{max}(2\theta = 31.8°)$ | |
| Working Example 9 | 2046 | 63697 | 0.0321 | 1.0 |
| Working Example 10 | 3161 | 67435 | 0.0469 | 3.1 |
| Comparative Example 12 | 5977 | 66219 | 0.0903 | 6.5 |
| Comparative Example 13 | — | 175666 | — | 0.0 |
| Working Example 11 | 3310 | 167124 | 0.0198 | 2.2 |
| Comparative Example 14 | — | 60102 | — | 0.0 |
| Working Example 12 | 1016 | 59905 | 0.0170 | 1.1 |
| Working Example 13 | 2060 | 58581 | 0.0352 | 3.3 |
| Comparative Example 15 | — | 81200 | — | 0.0 |
| Working Example 14 | 1950 | 84150 | 0.0232 | 2.4 |
| Working Example 15 | 3400 | 78450 | 0.0433 | 4.5 |
| Comparative Example 16 | 1036 | 55300 | 0.0187 | 2.0 |
| Comparative Example 17 | 1128 | 44375 | 0.0254 | 2.7 |
| Comparative Example 18 | 1134 | 49256 | 0.0230 | 2.3 |
| Comparative Example 19 | 1232 | 52941 | 0.0233 | 2.3 |
| Comparative Example 20 | — | 48465 | — | 0.0 |
| Comparative Example 21 | — | 54541 | — | 0.0 |
| Working Example 16 | 1652 | 49188 | 0.0336 | 3.2 |

Regarding the sample (powder) of which the peak showing heterogeneous phase $A_sB_tO_u$ was identified near $2\theta=29.3°$ and of which the intensity ratio $v=I_{max}(2\theta=29.3°)/I_{max}(2\theta=31.8°)$, the ratio between the peak near $2\theta=29.3°$ showing heterogeneous phase $A_sB_tO_u$ and the main peak near $2\theta=31.8°$ showing the main (single) phase $ABO_3$ was calculated. The result is shown in Chart 3. Regarding the X-ray diffraction profile, a Reitveld Analysis was done (using analysis software by the Rigaku Corporation PDXL) to extrapolate the heterogeneous of phase $A_sB_tO_u$ and the abundance ratio w (weight percentage). The said analysis showed that one of the heterogeneous phases of $A_sB_tO_u$ is the tetragonal $A_6B_{10.8}O_{30}$. The abundance ratio w (the production ratio) is shown in Chart 3. Regarding the embodiment of this invention, said ratio was calculated from the peak-intensity ratio. Yet, it can be used whenever peak separation preferably is to be made.

Working Examples 1 to 16, as seen in Chart 2, show that electromechanical-coupling coefficient Kp, as evaluated by the impedance analyzer, meets the process-capability index of $C_{pk}>1.33$ as the condition of Kp≥0.4 of which Piezoceramic Composition 10 of favorable property can be obtained with a low percentage of defects. Therefore, as seen in Chart 1, in manufacturing Piezoceramic Composition 10 of the composition ratio of Working Examples 1 to 16, a favorably stable property is realized with little variability from lot to lot, thus making it possible to produce a high rate of non-defective goods made of Piezoceramic Composition 10.

On the other hand, Comparative Examples 1 to 4, 10, 11, 13 to 15, 20 and 21 did not identify the peak (of heterogeneous phase $A_sB_tO_u$) being near $2\theta=29.3°$. Nor did the above Comparative Examples meet the condition of the process capability index $C_{pk}>1.33$ under the standard of Kp≥0.4. Whilst Comparative Examples 5 to 8 and 12 identified the existence of heterogeneous phase $A_sB_tO_u$, as shown in Chart 3, yet the abundance ratio w was too high (z>6.0%), and the intensity ration v of the main peak was greater than 0.088. Whenever the abundance ratio of heterogeneous phase $A_sB_tO_u$ is too high and the intensity ratio v of the main peak is greater than 0.088, the amount of A-site defects is less, thus resulting in deterioration of the electrical property.

Comparative Example 9 identified the existence of heterogeneous phase $A_sB_tO_u$. Yet, it did not contain even a slight amount of the added metallic elements (Bi, Fe) other than K, Na, Li, Nb, Ta and Sb. Thus, the initial amount of A-site defects on the main (single) phase (the crystalline phase of the perovskite structure signified as $ABO_3$) was small and electromechanical-coupling coefficient Kp was less than 0.4, thus resulting in deterioration of the piezoelectric property.

Comparative Examples 16 to 19 identified heterogeneous phase $A_sB_tO_u$ and intensity ratio v of the main peak, thus showing that the abundance ratio of the heterogeneous phase was less than 0.088. Yet, electromechanical-coupling coefficient Kp was less than 0.4, which was not enough to secure sufficient electric property. Regarding Comparative Examples 16 to 19, the added amount of metallic elements was so excessive that the X-ray diffraction profile identified diffraction lines showing the existence of the heterogeneous phase as being near $2\theta=27.5°$, which seems to show that the presence of Fe—Sb oxide was caused by favorable Piezoceramic Composition 10 not being formed. Thus, preferably, the added amount of metallic elements should not exceed z (the composition ratio)=0.2. (See Chart 1)

As described above, Piezoceramic Composition 10 of Working Examples 1 to 16 is made to include heterogeneous phase $A_sB_tO_u$ of $A_6B_{10.8}O_{30}$ showing that the ratio of Element A to Element B is from the overall composition, and that the A/B ratio (as represented in Chart 1) was approximately 0.95 to 0.98, meaning that the B-site is rich (Element B is excessive). Piezoceramic Composition 10 of Working Examples 1 to 16 includes about two percent of the A-site defects on the main phase, which means that the A-site defects can no longer be produced. Yet, the heterogeneous phase $A_sB_tO_u$ as a by-product is produced. Regarding Piezoceramic Composition 10 of Comparative Examples 9 to 11, when the metallic elements such as Bi and Fe, other than K, Na, Li, Nb, Ta and Sb, are not added, the acceptable amount of A-site defects on the main phase prominently decreases. Contrarily, as for Piezoceramic Composition 10 of Working Examples 1 to 16, adding a light amount of Bi or Fe introduces a point defect, so that the acceptable amount of A-site defects can be increased appropriately by about two percent. When increasing the amount of A-site defects on the main phase of Piezoceramic Composition 10, the density of the sintered body increases, thereby enhancing electromechanical-coupling coefficient Kp to 0.4 or more. Whenever Element A deficiency is excessive, the acceptable amount of A-site defects stops at about two percent and is no longer produced, thus causing heterogeneous phase $A_sB_tO_u$ not to produce. Whenever Element A is further lacking, and the production ratio of heterogeneous phase $A_sB_tO_u$ increases (refer to Comparative Examples 5 to 7), the balance is lost, so that the amount of A-site defects on the main (single) phase is likely to decrease.

If Piezoceramic Composition 10 is produced by sintering with the amount of A-site defects being equivalent to the limiting point at which heterogeneous phase $A_sB_tO_u$ is not produced, the most preferable piezoelectric property will be obtained. However, it is difficult to produce Piezoceramic Composition 10 of a composition ratio near the limiting point at which heterogeneous phase $A_sB_tO_u$ is not produced. When producing Piezoceramic Composition 10, the $K_2CO_3$ potassium powder of a high-moisture absorbency easily leads to weighing errors and causes potassium scattering whilst sintering, thus causing unevenness in the composition ratio of Piezoceramic Composition 10. Especially whilst mass-producing Piezoceramic Composition 10, due to unevenness of the firing temperature and the atmosphere within the firing furnace, it is difficult to control the sintering of all the Piezoceramic Composition 10 with the amount of A-site defects near about two percent. Also, if unevenness is caused in the composition ratio (for example, composition ratio A/B is 0.98 to 0.99) so that heterogeneous phase $A_sB_tO_u$ is not produced (i.e. if there is unevenness in the composition ratio of Comparison Examples 3 and 4), such fluctuation of the composition ratio will directly affect the increase-decrease rate of the amount of A-site defects. Therefore, regarding Comparative Examples 3 and 4, repeatability of the piezoelectric property and of the unevenness in the production lots will deteriorate. Contrarily, regarding Piezoceramic Composition 10 of Working Examples 1 to 16, the whole composition shows it to be B-site rich, that is A/B=0.95 to 0.98 (Element B is excessive). Therefore, repeatability of the piezoelectric property is present, so that an industrially stable piezoelectric property is obtained.

Eventually, the following effects can be achieved by the embodiments of this invention.

(1) Piezoceramic Composition 10 of Working Examples 1 to 16 of the embodiment of this invention has a composition ratio including heterogeneous phase $A_sB_tB_tO_u$, with the intensity ratio v of the diffraction intensity $I_{max}$ ranging at $0 < v \leq 0.088$ (see Chart 3). The other heterogeneous phase $A_6B_{10.8}O_{30}$ is generated with a weight ratio w of $1\% < w \leq 6.0\%$. This makes it possible to obtain Piezoceramic Composition 10 of a favorable property and of a radial electromechanical-coupling coefficient Kp of 0.4 or more, thereby making it an industrially stable piezoelectric property to obtain Piezoceramic Composition 10 of a process capability index $C_{pk}$ of 1.33 or more against the product standard of electromechanical-coupling coefficient Kp 0.4 or more. Whenever unevenness occurs in Piezoceramic Composition 10, the production ratio of heterogeneous phase $A_sB_tO_u$, which affects the property less, will fluctuate, though fluctuation of the A-site defects on the main (single) phase will be reduced. In other words, due to irregular sintering and formula-deviation caused by unevenness of temperature and the atmosphere within the firing furnace, the production ratio of heterogeneous phase $A_sB_tO_u$, which affects the property less, becomes moderate, thus controlling formula-deviation of the A/B ratio on the main (single) phase (the crystalline phase of the perovskite structure signified as $ABO_3$), which greatly affects the sintering and the property of Piezoceramic Composition 10, in that it can be entirely sintered within the firing furnace to the state thereof that the A-site defects on the main (single) phase is nearly maximum, thereby reducing the property of unevenness of the Piezoceramic Composition 10 so that it can be mass-produced at a high percentage of efficiency.

(2) Regarding Piezoceramic Composition 10 of Working Examples 1 to 16 of the embodiment (of this invention), whenever it is entirely of Working Example 1, the metallic elements Bi and Fe are added to the composition ratio z ranging at $0 < z \leq 0.02$, thus obtaining Piezoceramic Composition 10 of a good electrical property even if Ta of Element B is lacking. Ta is a relatively costly element compared to the other B Elements Nb or Sb, so that producing Piezoceramic Composition 10 without Ta reduces manufacturing cost. Especially, Piezoceramic Composition 10 of Working Examples 6, 9, 11 and 12 was formulated without Ta, so that heterogeneous phase $A_6B_{10.8}O_{30}$ was of the weight (w) ratio ranging at $1.0\% \leq w \leq 2.2\%$, with the electromechanical-coupling coefficient Kp expected to be 0.48 or more but actually determined being 0.0008 or less, thus controlling the property of unevenness and thereby increasing the process capability index $C_{pk}$ to 1.33 or more.

(3) Piezoceramic Composition 10 of Working Examples 1 to 16 of the embodiment (of this invention) contains Li as an Element A against K and Na at the rate of 1/10 or less. Thus, with Li being a relatively costly material, reducing the rate of Li to 1/10 or less further reduces the cost of manufacturing Piezoceramic Composition 10.

The Second Embodiment

The second embodiment of this invention described hereinafter is the method for manufacturing Piezoceramic Composition 10. Regarding the second embodiment, the calcined powder obtained after temporarily firing it undergoes an XRD analysis, with a composition adjustment then being done based on the result of the analysis. Below is described the method for manufacturing the embodiments of this invention.

Figure 3:
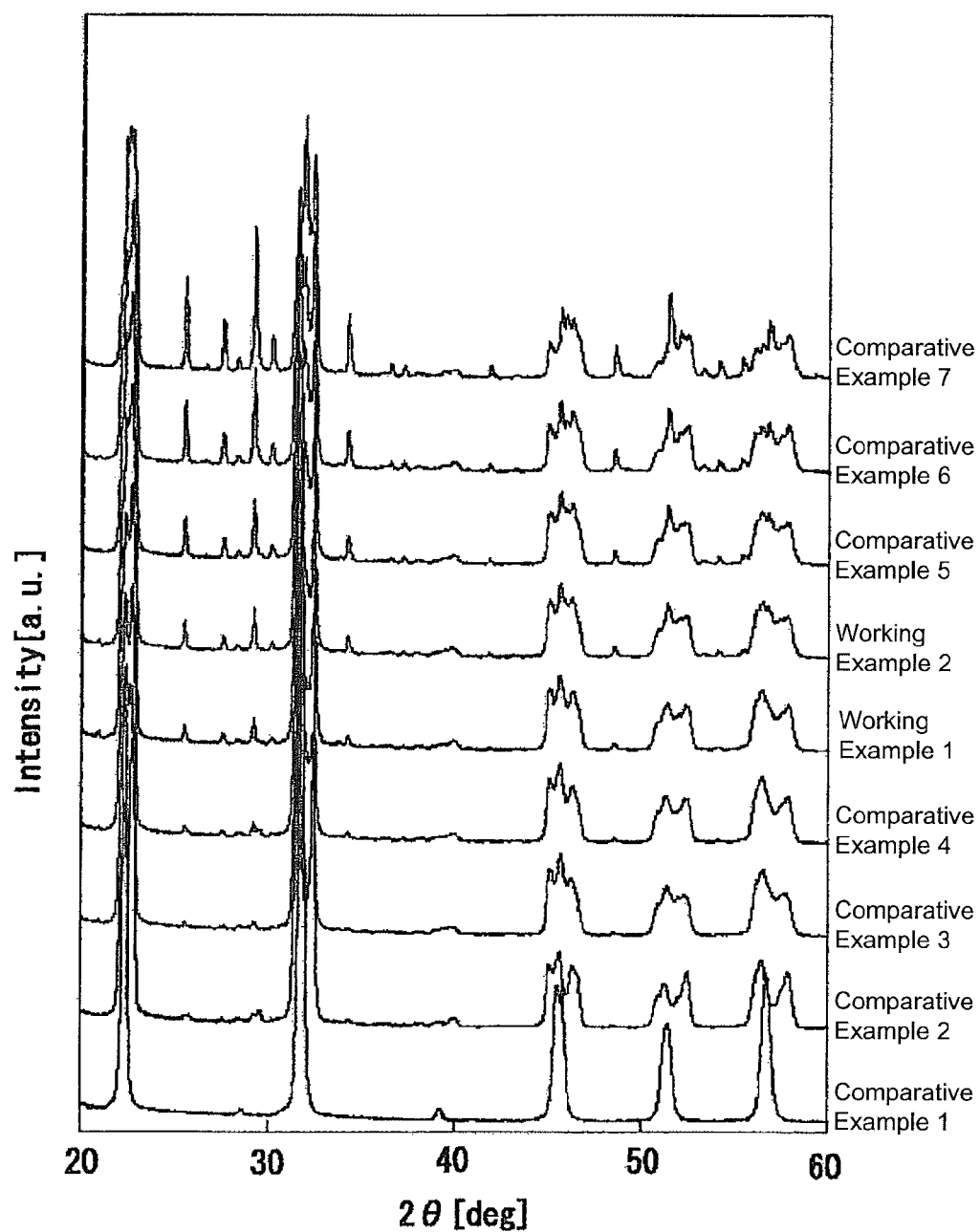
FIG. 3 is a graph describing the X-ray diffraction profile of the calcined powder of Embodiments 1 and 2, as well as Comparative Examples 1 to 7.

Firstly, as of the first embodiment, the base powder containing the metallic elements is mixed to obtain slurry. After drying, the slurry is calcined for three hours at 900 degree Celsius (the calcined process). The composition obtained by this calcining is crushed in a mortar to obtain a powder 10 μm or less in diameter. Then, the powder undergoes an XRD analysis to obtain an X-ray diffraction profile (the X-ray diffraction process). The measuring method of the XRD analysis is the same as that of the first embodiment. FIG. 3 shows examples of the X-ray diffraction profile of the calcined powder produced according to the composition ratio of Working Examples 1 and 2 and Comparative Examples 1 to 7.

Based on the X-ray diffraction profile, composition adjustment is done by dispensing the heterogeneous calcined powders to obtain the desired production ratio of heterogeneous phase $A_sB_tO_u$. Then, actual sintering is done at 1000 to 1200 degrees Celsius.

Regarding the material system of the embodiment of this invention, in temporarily sintering the prepared composition at 800 degrees Celsius to make it B-site excessive, little unreacted material remains. The crystalline phase $ABO_3$ may include many compositions, yet heterogeneous phases $A_6B_{10.8}O_{30}$, $A_4B_6O_{17}$ or the like will be produced depending on the balance of the entire ratio of A/B. If no unreacted material remains, compositional unevenness caused by the scattering of Element A (e.g. potassium) will be reduced after the temporarily sintering process. Thus, there seems to be a high correlation between the production ratio of heterogeneous phase $A_sB_tO_u$ of the calcined powder and the production ratio of heterogeneous phase $A_sB_tO_u$ of the sintered body obtained after sintering. Therefore, the measurements of the X-ray diffraction profile of the calcined powder can predict whether or not piezoelectric property is properly provided when Piezoceramic Composition 10 is produced using the calcined powder.

The result of the X-ray diffraction profile, using the calcined powder, predicts that the production ratio of heterogeneous phase $A_sB_tO_u$ will be outside the favorable range, thus worsening the piezoelectric property, so that a composition adjustment should be done to make it of the appropriate ratio A/B. Specifically, as shown in Charts 1 to 3, let us say for example that the calcined powder of Comparative Examples 2 and 5 are produced. The X-ray diffraction of the calcined powder predicts that said powder of Comparative Example 2 would not contain heterogeneous phase $A_sB_tO_u$, thus keeping the piezoelectric property poor.

First blend the two calcined powders mentioned above at the ration of 1:1 by weight, and ball-mill the mixture for six hours. Then, add a binder and polyvinyl alcohol to pelletize the mixture. After pelletization, the manufacturing process is the same as that of the aforementioned embodiment (of Working Examples 1 to 16).

Figure 4:
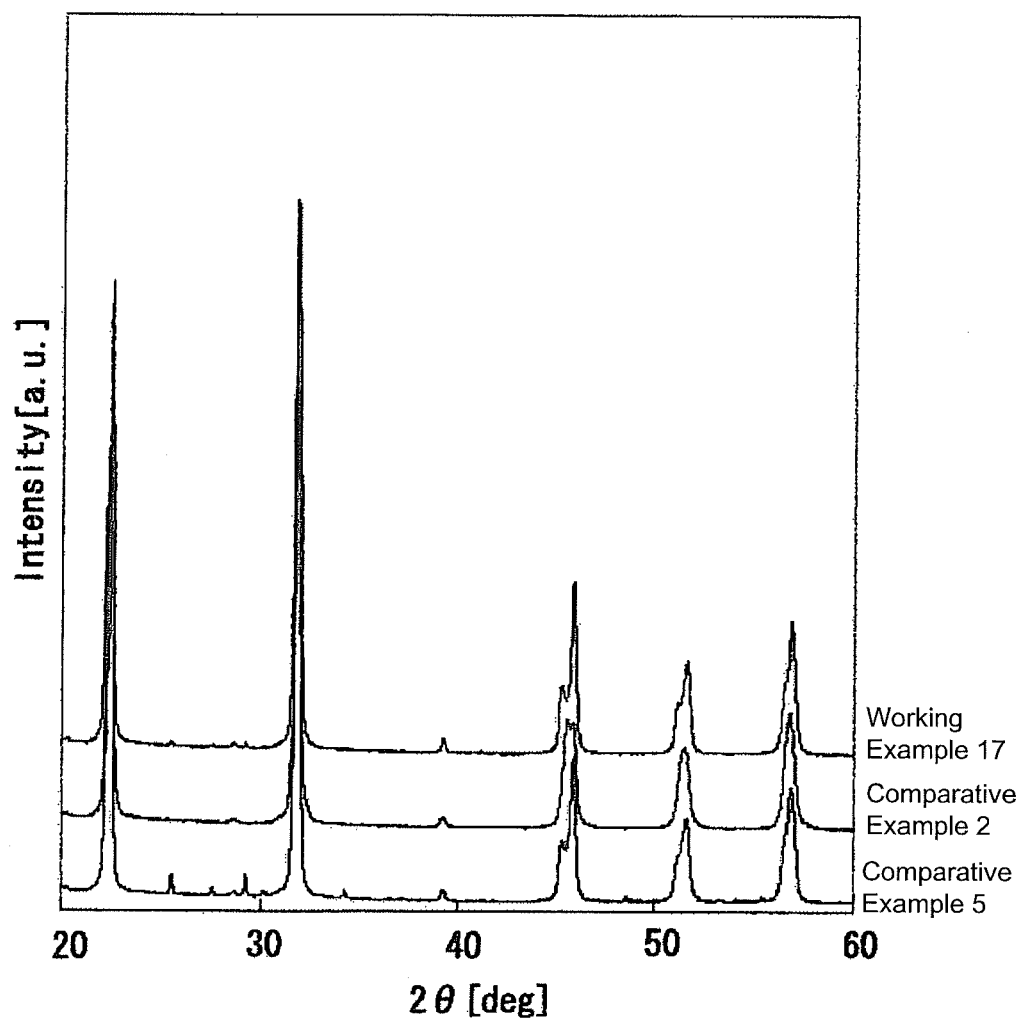
FIG. 4 is a graph describing the X-ray diffraction profile of the piezoceramic composition powder sample of Embodiment 17, as well as Comparative Examples 2 and 5.

Let Piezoceramic Composition 10 as produced above be as Working Example 17 and its X-ray diffraction profile be as shown in FIG. 4. Based on the X-ray diffraction profile, the presumed result of the production ratio of heterogeneous phase $A_sB_tO_u$ is shown in Chart 4, and its piezoelectric property is shown in Chart 5.

CHART 4

| | Intensity ratio of the XRD diffraction peak | | | $A_6B_{10.8}O_{30}$ |
|---|---|---|---|---|
| | $I_{max}$ (2θ = 29.3°) | $I_{max}$ (2θ = 31.8°) | $v = I_{max}(2θ = 29.3°)/ I_{max}(2θ = 31.8°)$ | production ratio w (wt. %) |
| Working Example 17 | 2831 | 72026 | 0.0393 | 1.8 |

CHART 5

| | Electrical property at 25 degrees Celsius (° C.) | | | Unevenness property of the same lot Standard deviation of Kp | Process Capability Index $C_{pk}$ |
|---|---|---|---|---|---|
| | Kp | $\epsilon_{33}^T/\epsilon_0$ | Tan δ | | |
| Working Example 17 | 0.463 | 1539 | 0.0180 | 0.0008 | 26.25 |

Piezoceramic Composition 10, as produced with the calcined powder of Comparative Examples 2 and 5, did not provide favorable piezoceramic property. Contrarily, Working Example 17 that was produced by blending the calcined powders of Comparative Examples 2 and 5 shows that production ratio w of heterogeneous phase $A_sB_tO_u$ is 1.8% by weight that is within the appropriate range. Thus, Working Example 17 confirms that the electromechanical-coupling coefficient Kp is 0.4 or more and is of favorable piezoelectric property and has a high process capability index $C_{pk}$.

In manufacturing the embodiment of this invention according to the above method, it can be predicted, due to compositional unevenness occurring in the calcining stage, that it will be impossible to obtain Piezoceramic Composition 10 of favorable piezoelectric property. Yet, even if some factor causes a production lot of calcined powder to be of compositional unevenness, another calcined powder can be appropriately blended with the original powder to enable it to be efficiently used so that said Piezoceramic Composition 10 is not wasted.

Each embodiment of this invention can be modified, as below.

Working Examples 1 to 17 of each embodiment of this invention include but do not limit Element A and the elements K (potassium), Na (sodium) and Li (lithium) and preferably comprise Element A and one or more of them.

Each embodiment includes but does not limit the heterogeneous phase $A_sB_tO_u$ to just the crystalline phases $A_6B_{10.8}O_{30}$ and $A_4B_6O_{17}$ as heterogeneous phase $A_sB_tO_u$, but also include: (a) $A_6B_{10.88}O_{30}$, (b) $A_{5.75}B_{10.85}O_{30}$, (c) $A_{2.6}B_{11.6}O_{30}$, (d) $A_3B_8O_{21}$, (e) $A_2B_8O_{21}$ or the like. In other words, heterogeneous phase $A_sB_tO_u$ is an oxidant, signified as composition formula $A_sB_tO_u$ (s, t and u are molar ratio) and contains Element B at the ratio of 1.5 times or more but less than 4.0 times of Element A.

Of the second embodiment of this invention, composition adjustment is done but is not limited for the purpose in obtaining the desired production ratio of heterogeneous phase $A_sB_tO_u$. For example, a further composition adjustment can be done to obtain the desired intensity of the main peak of heterogeneous phase $A_sB_tO_u$.

The second embodiment of this invention provides an example of the calcined powder being blended at the A/B ratio (of 1.00 as in Comparative Example 2 and of 0.94 is in Comparative Example 5). However, the ingredients used for a composition adjustment include not only $K_2CO_3$, $Na_2CO_3$, $Li_2CO_3$, $Nb_2O_5$, $Ta_2O_5$, $Sb_2O_3$ or the like, which are used as the base powder, but also the chemical compounds $A_6B_{10.8}O_{30}$, $A_4B_6O_{17}$ or the like, which are obtained by temporarily sintering after preparing and mixing the above materials.

Each embodiment of this invention contains the additional metallic elements of Bi and Fe in proportion of 1:1, which ratio can be accordingly modified. Other metallic elements include Cr, Mn, Ni, Co, Cu, Zn, Sr, Mo, Ag, Ba or the like. Furthermore, a combination of elements selected from those above can be added to Piezoceramic Composition 10 to obtain the same effect of the aforementioned embodiments.

Besides the technical ideas described in this invention, other technical ideas about each embodiment are described hereinafter.

(1) Piezoceramic composition according to a first aspect of the invention is characterized in that as the aforementioned Element A, the elements K, Na and Li are comprised.

(2) Piezoceramic composition according to a second aspect of the invention is characterized in that as the aforementioned Element A, the element Li is comprised in proportion of 1/10 or less as compared to the elements K and Na.

(3) Piezoceramic composition according to a third aspect of the invention is characterized in that it is an alkaline-niobate based composition comprising at least Nb as the aforementioned Element B as selected from among Nb, Ta and Sb.

(4) Piezoceramic composition according to a fourth aspect of the invention is characterized in that the aforementioned metallic elements Bi and Fe are in proportion of 1:1.

(5) Piezoceramic composition according to a fifth aspect of the invention is characterized in that it comprises Elements A and B at the A/B ratio of 0.95 or more but less than 0.98.

(6) Piezoceramic composition according to a sixth aspect of the invention is characterized in that it is produced at the aforementioned ratio of $1.0\% \leq w \leq 2.2\%$ by weight.

(7) Piezoceramic composition according to a seventh aspect of the invention is characterized in that it comprises the aforementioned additional metallic elements of composition ratio z ranging at $0.04 \leq z \leq 0.16$.

(8) The method for manufacturing piezoceramic composition according to an eighth aspect of the invention is characterized in that the aforementioned composition-adjustment process is done by blending calcined powder of a high production ratio with that of a low production ratio on the different phase.

(9) The method for manufacturing piezoceramic composition according to a ninth aspect of the invention is characterized in that the aforementioned adjustment process (composition adjustment) is done upon determining the desired production ratio of heterogeneous phase $A_sB_tO_u$ based on the X-ray diffraction profile.

(10) The method for manufacturing piezoceramic composition according to a tenth aspect of the invention is characterized in that a composition adjustment is done to obtain the intensity ratio v of the diffraction intensity $I_{max}$ (2θ=29.3°) of the peak showing the heterogeneous phase near 2θ=29.3° and to obtain the diffraction intensity $I_{max}$ (2θ=31.8°) of the main peak showing the main (single) phase near 2θ=31.8° and for v to range at $0<v \leq 0.088$.

(11) Piezoceramic composition according to an eleventh aspect of the invention is characterized in that the heterogeneous phase of the crystalline structure, which does not belong to the perovskite structure and is signified as formula $A_sB_tO_u$ (s<t<u), is a tungsten bronze-type crystalline structure.

DESCRIPTION OF REFERENCE SIGNS

10: Piezoceramic composition

What is claimed is:

1. A piezoceramic composition containing a crystalline phase of a perovskite structure having a main single phase signified as formula $ABO_3$,
    with element A consisting of one or more elements selected from among K (potassium), Na (sodium) and Li (lithium) and
    with element B consisting of one or more elements selected from among Nb (niobium), Ta (tantalum) and Sb (antimony), and
    wherein a Reitveld Analysis is conducted by obtaining an X-ray diffraction profile of a powder sample of the piezoceramic composition that is crushed until the particles of the piezoceramic composition are 10 μm or less in diameter, the X-ray diffraction profile having a diffraction peak indicating the presence of the main single phase as well as a heterogeneous phase of a crystalline structure signified as formula $A_sB_tO_u$, wherein s, t, and u are molar ratios and satisfy the relationship (s<t<u), $1.5 \leq t/s < 4.0$, the heterogeneous phase indicative of a tungsten bronze-type crystalline structure, the X-ray diffraction profile showing an intensity ratio (v)=$I_{max}$ (2θ=29.3°)/$I_{max}$ (2θ=31.8°) and defined as $0<v \leq 0.088$, with the X-ray diffraction profile indicating that the heterogeneous phase is near 2θ=29.3° and that the main peak diffraction intensity is near $I_{max}$ (2θ=31.8°).

2. The piezoceramic composition according to claim 1, characterized in that the heterogeneous phase is an oxide signified as $A_6B_{10.8}O_{30}$ of a weight ratio (w) of $0\%<w \leq 6.0\%$.

3. The piezoceramic composition according to claim 1, further comprising one or more additive elements selected from the group consisting of Fe, Bi, Cr, Mn, Ni, Co, Cu, Zn, Sr, Mo, Ag, Ba as part of the piezoceramic composition present in an amount to increase A-site defects in the main phase.

4. The piezoceramic composition according to claim 3, comprising added elements Bi (bismuth) and Fe (iron), such that formula $ABO_3$ further comprises (1−z) $ABO_3$+z $(0.5Bi_2O_3+0.5Fe_2O_3)$ of which the total composition ratio is one and z ranges at $0<z \leq 0.02$.

\* \* \* \* \*